United States Patent [19]
Suzuki

[11] Patent Number: 5,995,220
[45] Date of Patent: Nov. 30, 1999

[54] SEMICONDUCTOR PACKAGE INSPECTION APPARATUS

[75] Inventor: Yasuyoshi Suzuki, Fujisawa, Japan

[73] Assignee: Komatsu, Ltd., Tokyo, Japan

[21] Appl. No.: 09/252,473

[22] Filed: Feb. 18, 1999

[30] Foreign Application Priority Data

Feb. 19, 1998 [JP] Japan .................................. 10-037440

[51] Int. Cl.⁶ ............................. G01N 21/88; H04N 7/18; G06K 9/03
[52] U.S. Cl. ...................... 356/237.5; 356/394; 348/126; 382/145; 382/146
[58] Field of Search ............................... 356/237.5, 394; 348/93, 87, 126; 382/145–151

[56] References Cited

U.S. PATENT DOCUMENTS

| | | | |
|---|---|---|---|
| 5,030,008 | 7/1991 | Scott et al. | 356/394 |
| 5,039,868 | 8/1991 | Kobayashi et al. | 356/376 |
| 5,298,963 | 3/1994 | Moriya et al. | 356/237.5 |
| 5,528,371 | 6/1996 | Sato et al. | 356/394 |

FOREIGN PATENT DOCUMENTS

62-127617  6/1987  Japan ...................................... 356/394
2-231510   9/1990  Japan .

*Primary Examiner*—Frank G. Font
*Assistant Examiner*—Zandra V. Smith
*Attorney, Agent, or Firm*—Varndell & Varndell, PLLC

[57] ABSTRACT

A semiconductor package inspection apparatus comprises single photographic device disposed above the semiconductor package, and comprises light splitter for splitting light in different directions according to three different wavelength ranges in the light; and three image pickup units for separately photographing light of the three wavelength ranges which has been split by the light splitter; lighting device comprising first lighting for inspecting leads of the semiconductor package; second lighting for inspecting marks printed on top face of the semiconductor package; and third lighting for inspecting defects of the semiconductor package, the first, second and third lightings being disposed at locations different from each other, and having wavelength ranges into which the light has been split by the light splitter, and inspection device for simultaneously operating the first, second and third lightings of the lighting device and the three image pickup units of the photographic device to inspect leads of the semiconductor package, marks printed on top face of the semiconductor package and defects in the semiconductor package based on the photographic data from the three image pickup units.

2 Claims, 4 Drawing Sheets

SEMICONDUCTOR PACKAGE INSPECTION APPARATUS

BACKGROUND OF THE INVENTION

1. Field of the Invention

This invention relates to a semiconductor package inspection apparatus for inspecting semiconductor packages of various types, such as PGA (pin grid array), QFP (quad flat package), QFJ (quad flat J-leaded package), SOP (small outline package), SOJ (small outline J-leaded package), DIP (dual inline package) and BGA (ball grid array), with regard to various items for inspection, such as mislocation, pitch, coplanarity and tip misalignment of the terminals; missing, blurred and mislocated characters in marks printed on semiconductor package surfaces; and internal cavities in semiconductor package surfaces.

2. Description of the Related Art

Items for inspection of semiconductor packages of types such as PGA, QFP, QFJ, SOP, SOJ, DIP and BGA include:

(1) inspection for location, pitch, coplanarity and tip alignment of terminals (2) inspection for missing, blurred or mislocated characters in marks (such as manufacturing number and manufacturer name) printed on semiconductor package surfaces (3) inspection for defects such as internal cavities formed in semiconductor package surfaces.

Nowadays, methods which employ photographic devices such as CCD cameras are predominantly used for these inspections.

In conducting such inspections using photographic data from cameras, lighting conditions are crucial, and there is a proper lighting location for each inspection item. Depending on the inspection items, a single camera may suffice in some inspection items, while in other inspection items a plurality of cameras must be disposed in different locations.

Thus, since there is a proper lighting location for each inspection item, there are plural proper lighting locations for all inspection items. If all lights at plural lighting locations are lit simultaneously, lighting cannot be conducted in an optimal manner for photographing each inspection item, regardless of whether a single camera is used or a plurality of cameras is used for photographing.

Therefore, the practice has been that, when conducting a terminal inspection, only the lighting and camera corresponding to the terminal inspection are operated; when conducting a mark inspection, only the lighting and camera corresponding to the mark inspection are operated; and when conducting a defect inspection for internal cavities and the like, only the lighting and camera corresponding to this inspection are operated.

In the conventional art, the lighting and cameras for each inspection item cannot be operated simultaneously, and have therefore been operated sequentially one inspection item after another. Thus, photography has been time consuming, making it impossible to perform efficient semiconductor package inspections.

SUMMARY OF THE INVENTION

The present invention has been made with the foregoing in view, and has as an object to provide a semiconductor package inspection apparatus capable of perform inspections at an improved speed.

According to this invention, the aforestated object is achieved through a semiconductor package inspection apparatus which comprises single photographic means disposed above a semiconductor package and comprising light-splitting means for splitting incident light in different directions in accordance with three different wavelength ranges in the incident light; and three image pickup means for separately photographing light of the three wavelength ranges which has been split by the light-splitting means; lighting means comprising first lighting for inspecting leads of the semiconductor package; second lighting for inspecting marks printed on top face of the semiconductor package; and third lighting for inspecting defects of the semiconductor package, wherein the first, second and third lightings are disposed at locations different from each other, and have wavelength ranges into which the light has been split by the light-splitting means, and inspection means for simultaneously operating the first, second and third lightings of the lighting means and the three image pickup means of the photographic means so as to inspect leads of the semiconductor package, marks printed on a top face of the semiconductor package and defects in the semiconductor package on the basis of photographic data acquired from the three image pickup means.

The semiconductor package inspection apparatus according to this invention is so constructed that there is provided over a semiconductor package a single photographic apparatus comprising a light-splitting optical system, such as a dichroic prism, capable of splitting light in different directions in accordance with three different wavelength ranges, and three photographing means for separately photographing light of these wavelength ranges; there is also provided lighting means comprising first lighting for inspecting leads of the semiconductor package, second lighting for inspecting marks printed on the top face of the semiconductor package, and third lighting for inspecting defects of the semiconductor package, the wavelength range of these three lightings being respectively assigned corresponding to the three wavelength ranges of the photographic apparatus; and these three photographing means and lightings are operated simultaneously, whereby the photographic processes needed for inspections of leads, marks printed on the top faces of semiconductor packages, and defects in semiconductor packages can be conducted simultaneously, thus reducing the photographing time and enhancing efficiency in the semiconductor package inspections.

In addition, the photographic apparatus is made in a single unit so that the space required by the photographic and optical systems can be reduced and adjustment of the optical system can be simplified.

DESCRIPTION OF THE PREFERRED EMBODIMENTS

Embodiments of this invention are described below making reference to the accompanying drawings.

Figure 1:
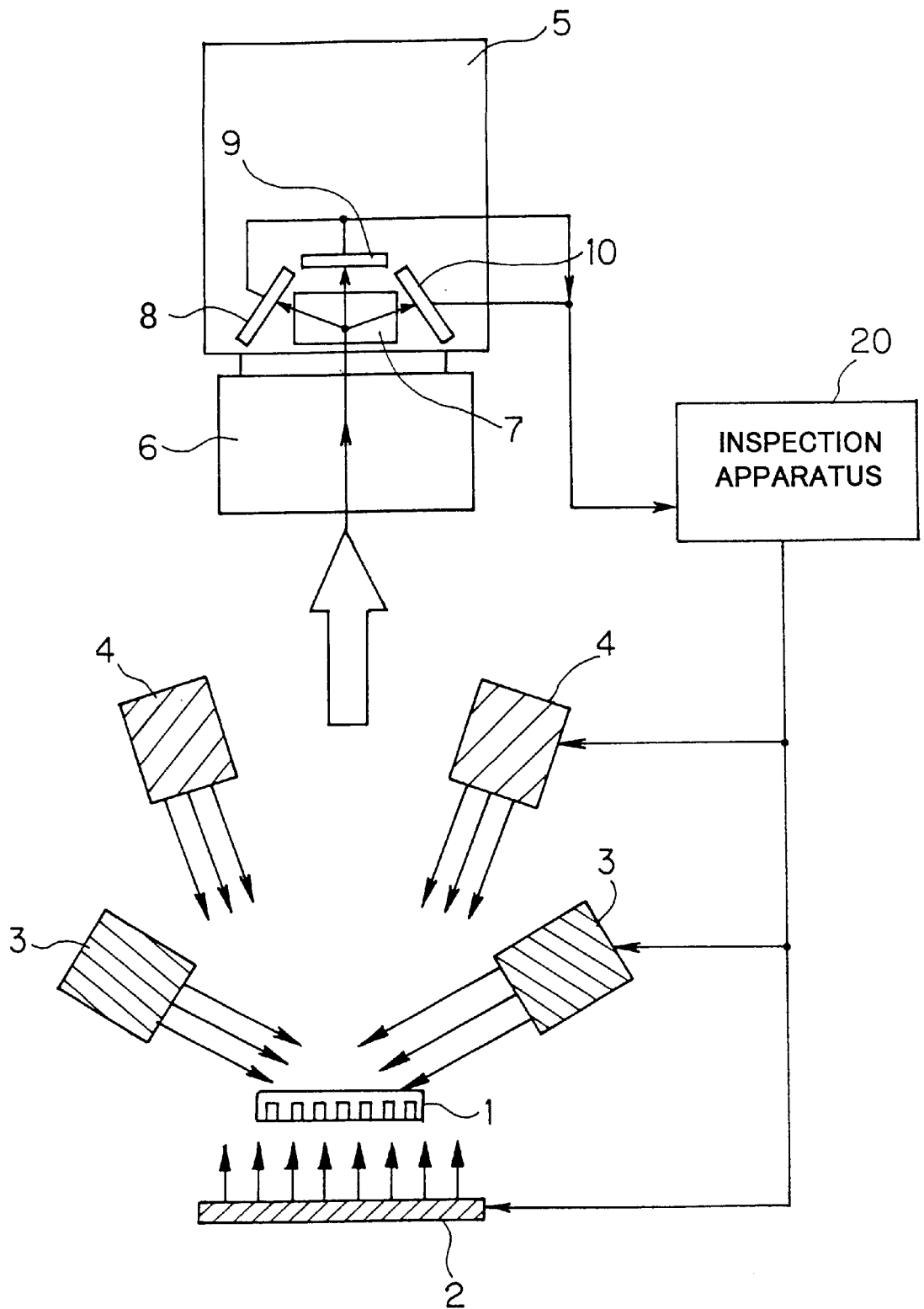
FIG. 1 is a diagram depicting an embodiment of this invention.

FIG. 1 is a conceptual depiction of an embodiment of this invention. In this embodiment, a semiconductor package to be inspected is an SOP.

Referring to FIG. 1, a lighting 2 which is used to inspect leads of a semiconductor package 1 is arranged below the semiconductor package 1 so as to light the semiconductor package 1 from below. Arranged inclined above the semiconductor package 1 are a plurality of lighting 3 which are used to inspect marks printed on the semiconductor package 1 so as to light the package 1 from above and from the perimeter in an inclined manner. Further, a plurality of lighting 4 which is used to inspect internal cavities and the like in the package 1 are disposed in inclined manner from further above the mark inspection lighting 3 and from the perimeter. That is, lighting 2–4 are disposed in locations optimal for each particular inspection item.

The wavelength of each lighting 2–4 is determined corresponding to that of respective one of the three primary colors (RGB) of light (R: red—wavelength about 640 nm; G: green—wavelength about 530 nm; B: blue—wavelength about 470 nm). Specifically, the lead inspection lighting 2 is assigned blue, the mark inspection lighting 3 red, and the internal cavity inspection lighting 4 green.

A camera 5 is disposed so as to photograph the semiconductor package 1 from directly above; it houses therein a lens system 6, a dichroic prism 7 that serves as the light-splitting optical system, and three CCD cameras 8, 9 and 10.

The dichroic prism 7 is composed of one or more multilayer film prisms that utilize the basic principle of a multilayer film interference filter, and has the function of splitting incident light in different directions in accordance with the three different wavelength ranges.

Specifically, the light splitting process is here conducted in such a way that incident light of approximately 470 nm wavelength, corresponding to blue light, is directed onto the CCD camera 8, incident light of approximately 640 nm wavelength, corresponding to red light, is directed onto the CCD camera 9, and incident light of approximately 530 nm wavelength, corresponding to green light, is directed onto the CCD camera 10.

The CCD camera 8 has spectral sensitivity characteristics designed such that it is highly sensitive to the wavelength range corresponding to blue light, the CCD camera 9 has spectral sensitivity characteristics designed such that it is highly sensitive to the wavelength range corresponding to red light, and the CCD camera 10 has spectral sensitivity characteristics designed such that it is highly sensitive to the wavelength range corresponding to green light.

An inspection apparatus 20 controls lighting of the three lighting 2–4, and performs image processing using image data obtained by the three CCD cameras 8–10 to conduct semiconductor package 1 lead inspections, mark inspections, and package face defect inspections.

According to the configuration of the inspection apparatus 20, all of the three lighting 2–4 are lit simultaneously when conducting an inspection of the semiconductor package 1.

Specifically, images of the semiconductor package 1 created by illumination by the blue lighting 2, the red lighting 3 and the green lighting 4 are simultaneously directed into the camera 5 and split into light of the R, G and B wavelength ranges by the dichroic prism 7. The semiconductor package images that have been split into the R, G and B wavelength ranges are directed into the respective CCDs 8–10. As a result, the CCD 8 for blue wavelength (blue CCD 8) photographs the image of the semiconductor package 1 produced by illumination by the blue lighting 2, the CCD 9 for red wavelength (red CCD 9) photographs the image of the semiconductor package 1 produced by illumination by the red lighting 3, and the CCD 10 for green wavelength (green CCD 10) photographs the image of the semiconductor package 1 produced by illumination by the green lighting 4.

Figure 2A:
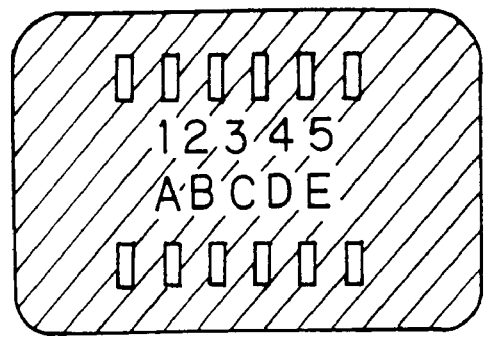
FIGS. 2(*a*), 2(*b*) and 2(*c*) illustrate images picked up by CCDs in the embodiment of FIG. 1.
Figure 2B:
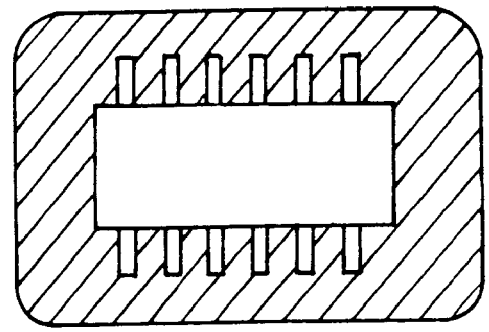
Figure 2C:
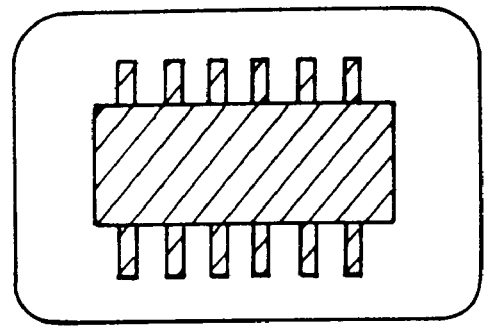

FIG. 2(a) shows an image for the mark inspection photographed by the red CCD 9, FIG. 2(b) shows an image for the package (internal cavity) inspection photographed by the green CCD 10, and FIG. 2(c) shows an image for the lead inspection photographed by the blue CCD 8. Of these images, only the image for the lead inspection depicted in FIG. 2(c) is conducted with illumination from below the semiconductor package, so the semiconductor package image portion is shaded.

In the inspection apparatus 20, the image photographed by the blue CCD 8 is processed and inspected to detect lead mislocation, pitch, misaligned tips and the like; the image photographed by the red CCD 9 is processed and inspected to detect missing, blurred or mislocated characters in marks (such as manufacturing number and manufacturer name) printed on the semiconductor package surface; and the image photographed by the green CCD 10 is processed and inspected to detect defects such as internal cavities in semiconductor package surfaces.

According to this embodiment, there is arranged above the semiconductor package 1 the single camera 5 housing the dichroic prism 7 capable of splitting light in different directions in accordance with three different wavelength ranges corresponding to R, G and B and the three CCD cameras 8–10 each having high spectral sensitivity to one of these wavelength ranges. Further, there are provided, arranged at locations optimal for each particular inspection item, three lighting 2–4 that respectively emit light of the R, G and B wavelength ranges. These three CCD cameras 8–10 and lighting 2–4 are operated simultaneously, whereby the photographic processes needed for lead inspection, mark inspection and package defect inspection in the semiconductor package 1 may be conducted simultaneously, thus reducing the photographing time and affording efficient semiconductor inspection. Since the camera 5 is a single unit, the space required by the photographic and optical systems can be reduced, and adjustment of the optical system can be simplified.

According to the embodiment depicted in FIG. 1, the camera 5 is arranged directly above the semiconductor package 1, and thus height-wise information about the leads cannot be acquired, making it impossible to inspect the coplanarity of the leads.

Figure 3:
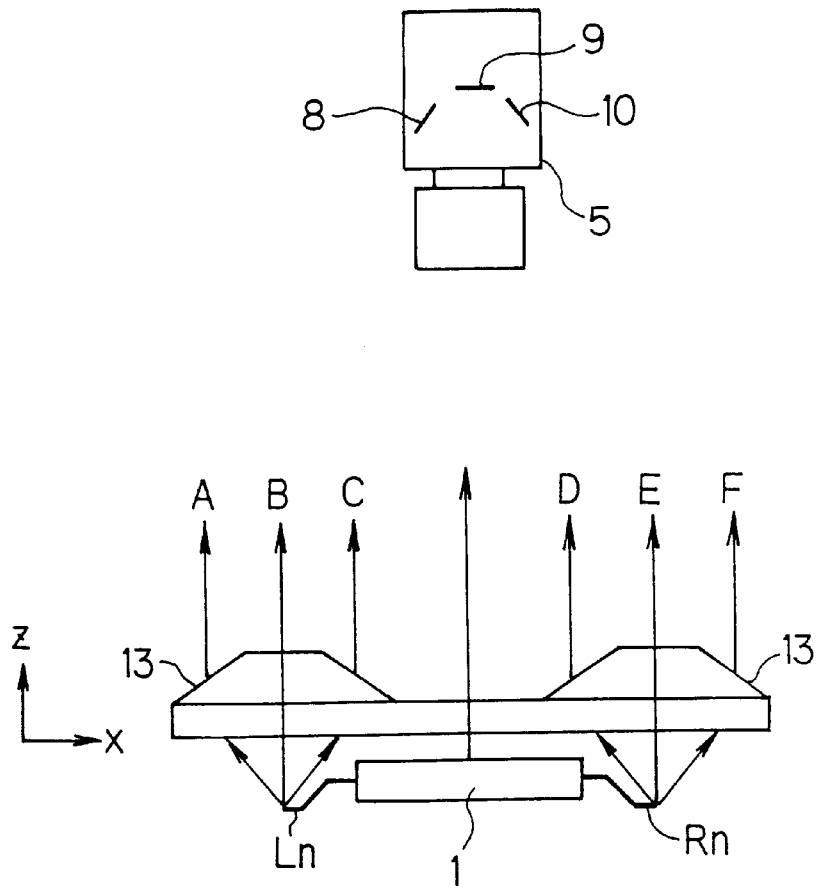
FIG. 3 is a diagram depicting another embodiment of this invention.

To make possible to inspect the coplanarity of the leads, two Dove prisms 13 are provided between the camera 5 and the semiconductor package 1 such that a gap is provided between them corresponding to the width of the top face of the semiconductor package 1 in the manner depicted in FIG. 3, for example. With these Dove prisms 13, the images of the tips of the leads of the semiconductor package 5 can be photographed from three different directions including skew upward directions in a single frame. Specifically, images of the left lead terminals L1–Ln of the semiconductor package 1 enter the camera 5 over optical paths A, B and C, while images of the right lead terminals R1–Rn enter the camera 5 over optical paths D, E and F.

Figure 4:
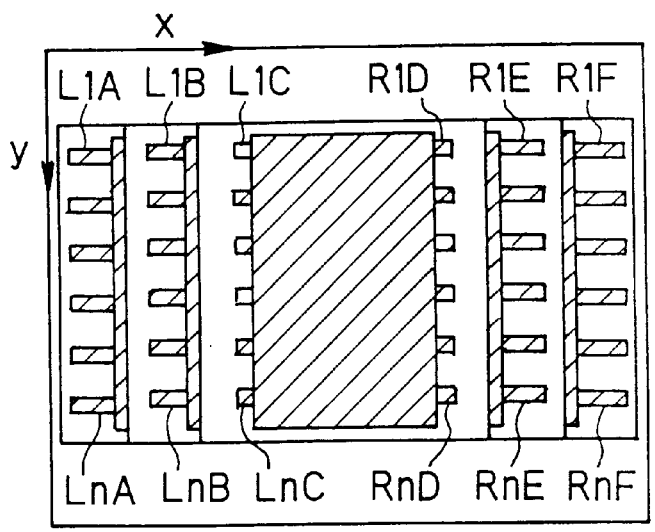
FIG. 4 illustrates a photographic image of lead terminals in the embodiment of FIG. 3.

FIG. 4 shows an image of the leads photographed by the blue CCD 8 housed in the camera 5. This single photographic image produced by the CCD 8 contains images L1A–LnA, L1B–LnB and L1C–LnC of the left lead terminals L1–Ln photographed through three optical paths A, B, C, and images R1D–RnD, R1E–RnE and R1F–RnF of the right lead terminals R1–Rn photographed in three optical paths D, E, F.

From this single image produced by the CCD 8, the inspection apparatus 20 determines x-coordinate displacements of the images of each lead tip at two positions out of the images of the lead tip at three positions, and, using the principle of triangulation, computes the z-coordinate of the tip of the lead.

With the gap provided between the two Dove prisms 13, which corresponds to the width of the top face of the semiconductor package 1, the image of the top face of the semiconductor package 1 is allowed to enter the camera 5 directly without passing though the prisms 13, and then enters the red CCD 9 and the green CCD 10 of the camera 5. Therefore, inspection for marks and inspection for internal cavities in the package can be made on the basis of photographic data from these CCDs 9 and 10.

Figure 5:
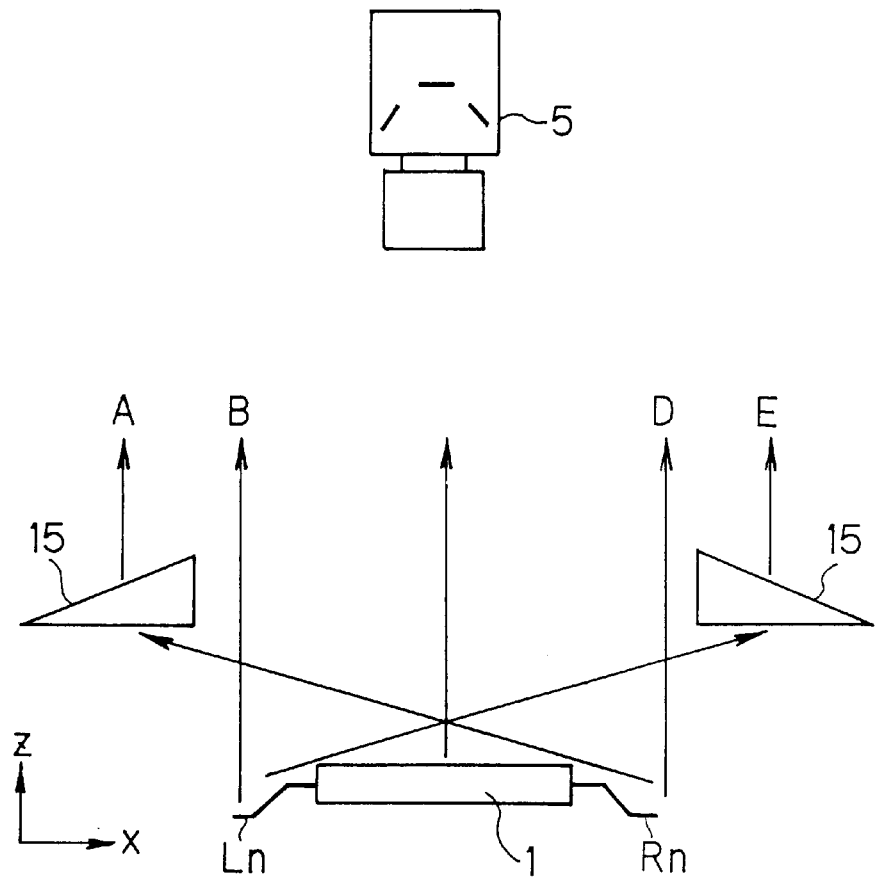
FIG. 5 is a diagram depicting still another embodiment of this invention.

FIG. 5 shows is a modification of FIG. 3 wherein two prisms 15 with a gap between them are provided in place of the two Dove prisms 13 as shown in FIG. 3. This allows images of the lead tips of the semiconductor package 5 to be photographed from two different directions including skew upward directions. Specifically, images of the left lead terminals L1–Ln of the semiconductor package 1 enter the camera 5 over optical paths B and E, while images of the right lead terminals R1–Rn enter the camera 5 over optical paths A and D.

Figure 6:
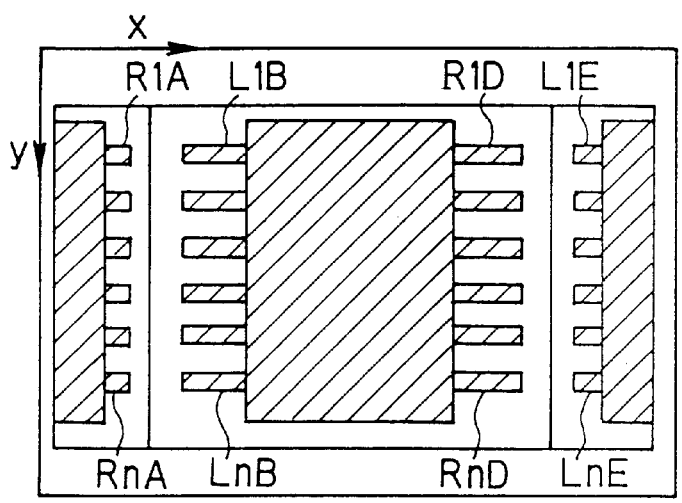
FIG. 6 illustrates a photographic image of lead terminals in the embodiment of FIG. 5.

FIG. 6 depicts a lead inspection image photographed by the blue CCD 8 of camera 5. This single photographic image produced by the CCD 8 contains the images of the left lead terminals L1–Ln photographed through the optical paths B and E (L1B–LnB and L1E–LnE), and the images of the right lead terminals R1–Rn photographed through the optical paths A and D (R1A–RnA and R1D–RnD).

From this single image produced by the CCD 8, the inspection apparatus 20 determines x-coordinate displacements of the images of each lead tip at two positions, and, using the principle of triangulation, computes the z-coordinate of the tip of the lead.

Here as well, a gap corresponding to the width of the top face of the semiconductor package 1 is provided between the prisms 15, allowing the mark inspection and the inspection for internal cavities in the package to be conducted simultaneously with the lead inspection in the same manner as that described above in connection with the configuration shown in FIG. 3.

In the foregoing embodiments, a dichroic prism is employed as the light-splitting optical system 7, but it would be possible to employ any other optical means, such as a dichroic mirror, provided that it has the ability to split light according to wavelength.

Further, in the foregoing embodiments, the present invention is applied to a semiconductor package of SOP, but could be employed for lead terminal inspection of any other type of semiconductor package, such as SOJ (small outline J-leaded package), PGA (pin grid array), QFP (quad flat package), QFJ (quad flat J-leaded package), or BGA (ball grid array).

What is claimed is:

1. A semiconductor package inspection apparatus comprising:

single photographic means disposed above a semiconductor package and comprising:
light-splitting means for splitting incident light in different directions in accordance with three different wavelength ranges in the incident light; and
three image pickup means for separately photographing light of the three wavelength ranges which has been split by the light-splitting means;

lighting means comprising:
first lighting for inspecting leads of the semiconductor package;
second lighting for inspecting marks printed on top face of the semiconductor package; and
third lighting for inspecting defects of the semiconductor package,
wherein the first, second and third lightings are disposed at locations different from each other, and have wavelength ranges into which the light has been split by the light-splitting means, and inspection means for simultaneously operating the first, second and third lightings of the lighting means and the three image pickup means of the photographic means so as to inspect leads of the semiconductor package, marks printed on a top face of the semiconductor package and defects in the semiconductor package on the basis of photographic data acquired from the three image pickup means.

2. The semiconductor package inspection apparatus according to claim 1, wherein the three wavelength ranges assigned to the photographic means and lighting means are wavelength ranges corresponding to red, blue and green.

* * * * *